United States Patent [19]

Thyes et al.

[11] 4,410,529
[45] Oct. 18, 1983

[54] NOVEL DIHYDROPYRIDAZINONES, THEIR PREPARATION AND THERAPEUTIC AGENTS CONTAINING THESE COMPOUNDS

[75] Inventors: Marco Thyes; Horst Koenig; Dieter Lenke, all of Ludwigshafen; Hans D. Lehmann, Hirschberg-Leutershausen; Josef Gries, Wachenheim, all of Fed. Rep. of Germany

[73] Assignee: BASF Aktiengesellschaft, Fed. Rep. of Germany

[21] Appl. No.: 272,992

[22] Filed: Jun. 12, 1981

[30] Foreign Application Priority Data

Jun. 13, 1980 [DE] Fed. Rep. of Germany ....... 3022176

[51] Int. Cl.$^3$ .................... C07D 237/04; A61K 31/50
[52] U.S. Cl. .................................. 424/250; 544/239; 562/456; 562/457
[58] Field of Search ........................ 424/250; 544/239

[56] References Cited

U.S. PATENT DOCUMENTS

| | | | |
|---|---|---|---|
| 3,824,271 | 7/1974 | Allen, Jr. et al. | 269/465 D |
| 3,888,901 | 6/1975 | Allen, Jr. et al. | 260/465 R |
| 4,011,321 | 3/1977 | Coates et al. | 424/250 |

FOREIGN PATENT DOCUMENTS

| | | |
|---|---|---|
| 113 | 1/1979 | European Pat. Off. ............ 544/239 |
| 1670158 | 12/1970 | Fed. Rep. of Germany . |
| 2123246 | 5/1971 | Fed. Rep. of Germany . |
| 2150436 | 4/1972 | Fed. Rep. of Germany . |
| 2304977 | 8/1974 | Fed. Rep. of Germany . |
| 2727481 | 1/1979 | Fed. Rep. of Germany . |

OTHER PUBLICATIONS

McEvoy et al., J. Med. Chem., 17 (1974); vol. 17; No. 3, pp. 281–286.

*Primary Examiner*—Mark L. Berch
*Attorney, Agent, or Firm*—Keil & Witherspoon

[57] ABSTRACT

Novel 6-(p-acylaminophenyl)-4,5-dihydro-3(2H)-pyridazinones, whose acyl radical is derived from a cycloalkylcarboxylic acid, processes for their preparation, pharmaceutical formulations containing these compounds, and their use as drugs in thrombo-embolic disorders and as anti-hypertensives.

3 Claims, No Drawings

NOVEL DIHYDROPYRIDAZINONES, THEIR PREPARATION AND THERAPEUTIC AGENTS CONTAINING THESE COMPOUNDS

The present invention relates to novel 6-(p-acylaminophenyl)-4,5-dihydro-3(2H)-pyridazinones, whose acyl radical is derived from a cycloalkylcarboxylic acid, to processes for their preparation, to pharmaceutical formulations containing these compounds, and to their use as drugs in thrombo-embolic disorders and as anti-hypertensives.

6-(Acylamino)-phenyl-4,5-dihydro-3(2H)-pyridazinones have been described in various publications. For example, German Laid-Open Application DOS No. 1,670,158 describes 6-(acylamino)phenyl-4,5-dihydro-3(2H)-pyridazinones which are unsubstituted in the 4- and 5-positions and which have blood pressure-lowering and anti-inflammatory properties. This publication gives alkanoyl and cycloalkylcarbonyl, of 5 to 7 carbon atoms in the ring, as examples of acyl in the acylamino group of the dihydropyridazinones. According to German Laid-Open Application DOS No. 2,123,246, 6-(p-aminoalkanoylaminophenyl)-4,5-dihydro-3(2H)-pyridazinones which are unsubstituted in the 4- and 5-positions have a blood pressure-lowering, coronary-dilating and anti-inflammatory action. German Laid-Open Application DOS No. 2,304,977 states that 6-(p-acylaminophenyl)-4,5-dihydro-3(2H)-pyridazinones which carry an alkyl group in the 4-position have cardiovascular and antiphlogistic properties. German Laid-Open Application DOS No. 2,150,436 and U.S. Pat. Nos. 3,824,271 and 3,888,901 describe 5-alkyl-substituted 6-alkanoylaminophenyl-4,5-dihydro-3(2H)-pyridazinones which lower the blood pressure. An article by F. J. McEvoy and G. R. Allen, Jr. (J.Med.Chem. 17 (1974), 281 et seq.) discloses that 4,5-dihydro-5-methyl-6-(p-trifluoroacetylaminophenyl)-3(2H)-pyridazinone lowers the blood pressure. Finally, 6-(p-alkanoylaminophenyl)-4,5-dihydro-3(2H)-pyridazinones in which alkanoyl is substituted by one or more halogen atoms, and which may or may not be 5-alkyl-substituted, have been proposed as drugs because of their thrombocyte aggregation-inhibiting and blood pressure-lowering properties (German Laid-Open Applications DOS 2,727,481 and DOS 2,854,191).

We have found that 6-(p-acylaminophenyl)-4,5-dihydro-3(2H)-pyridazinones of the general formula I

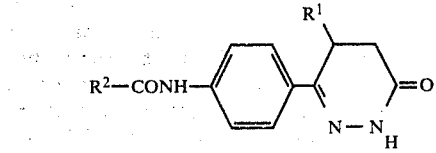

where $R^1$ is hydrogen or alkyl of 1 to 3 carbon atoms, and if $R^1$ is hydrogen, $R^2$ is cycloalkyl which has 3 or 4 carbon atoms in the ring and is unsubstituted or carries up to four substituents chosen from halogen and/or alkyl of 1 to 4 carbon atoms or, if $R^1$ is alkyl of 1 to 3 carbon atoms, $R^2$ is cycloalkyl which has 3 to 8 carbon atoms in the ring and is unsubstituted or carries up to four substituents chosen from halogen and/or alkyl of 1 to 4 carbon atoms, exhibit valuable pharmacological properties.

Alkyl $R^1$ is, in particular, methyl, ethyl or propyl.

If $R^1$ is hydrogen, $R^2$ is cycloalkyl which is unsubstituted or carries up to four substituents chosen from halogen atoms, such as chlorine, bromine and fluorine, and/or alkyl of 1 to 4 carbon atoms; specific examples are cyclopropyl, 1-methylcyclopropyl, 2-methylcyclopropyl, 2,2-dimethylcyclopropyl, 1,2,2-trimethylcyclopropyl, 2,2,3-trimethylcyclopropyl, 2,2,3,3-tetramethylcyclopropyl, 1-butylcyclopropyl, 1-chlorocyclopropyl, 2-bromocyclopropyl, 2,2-dichlorocyclopropyl, 2,2-dibromocyclopropyl, 2,2-dichloro-1-methylcyclopropyl, 2,2-dibromo-1-methylcyclopropyl, cyclobutyl, 1-methylcyclobutyl, 2-methylcyclobutyl, 3-methylcyclobutyl, 3,3-dimethylcyclobutyl, 1-propylcyclobutyl, 1-butylcyclobutyl, 3-tert.-butylcyclobutyl, 1-chlorocyclobutyl, 2-chlorocyclobutyl, 3-chlorocyclobutyl, 1-bromocyclobutyl, 3-bromocyclobutyl, 2,2,3,3-tetrafluorocyclobutyl, 3-chloro-3-methylcyclobutyl and 1-bromo-3,3-dimethylcyclobutyl.

If $R^1$ is alkyl, $R^2$ is cycloalkyl which is unsubstituted or carries up to four substituents chosen from halogen, such as chlorine, bromine and fluorine, and/or alkyl of 1 to 4 carbon atoms, specific examples being those mentioned above and also cyclopentyl, 1-methylcyclopentyl, 2,5-dimethylcyclopentyl, 1-chlorocyclopentyl, 1-bromocyclopentyl, 3-chlorocyclopentyl, 3,4-dichlorocyclopentyl, cyclohexyl, 1-methylcyclohexyl, 2-ethylcyclohexyl, 1-chlorocyclohexyl, 4-chlorocyclohexyl, 1,4-dichlorocyclohexyl, 3,4-dichlorocyclohexyl and cycloheptyl.

Preferred compounds are those where $R^1$ is hydrogen or methyl and, if $R^1$ is hydrogen, $R^2$ is cycloalkyl which has 3 or 4 carbon atoms in the ring and is unsubstituted or carries up to three substituents chosen from halogen and/or methyl, or, if $R^1$ is methyl, $R^2$ is cycloalkyl which has 3 to 6 carbon atoms in the ring and is unsubstituted or carries up to three substituents chosen from halogen and/or methyl.

Particularly preferred compounds, in respect of their effect, are those where $R^1$ is hydrogen or methyl and $R^2$ is cyclopropyl which is monosubstituted, disubstituted or trisubstituted by halogen, especially chlorine or bromine, and/or methyl.

The dihydropyridazinones of the formula I can be prepared by a process wherein a compound of the formula II

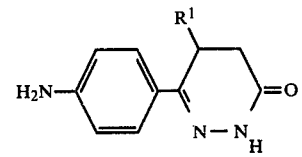

where $R^1$ has the meanings given for formula I, is reacted with an acylating agent of the formula III $$R^2COY \qquad \text{III,}$$

where $R^2$ has the meanings given for formula I and Y is OH, halogen, especially chlorine, lower alkoxy or $OCOR^2$, in a conventional manner.

In accordance with the meanings given for Y, advantageous acylating agents are the corresponding carboxylic acids, carboxylic acid halides, especially chlorides, carboxylic acid esters, especially methyl esters and ethyl esters, and corresponding carboxylic acid anhydrides.

The acylation is carried out under conventional conditions, as a rule using not less than an equimolar amount of the acylating agent, advantageously in the presence of a solvent, and in the presence or absence of an auxiliary base as an acid acceptor, at from 0° to 160° C., if appropriate at the boiling point of the reaction mixture, and, where necessary, under pressure.

Suitable solvents are those which are inert under the reaction conditions, such as aromatic hydrocarbons, eg. benzene or toluene, cyclic aliphatic ethers, eg. tetrahydrofuran or dioxane, or dialkylformamides, eg. dimethylformamide. Auxiliary bases used as acid acceptors are, advantageously, inorganic bases, such as sodium carbonate or potassium carbonate, sodium bicarbonate or potassium bicarbonate, or tertiary organic amines, such as triethylamine.

In another embodiment, the novel compounds of the formula I are obtained by a process wherein an acylamino compound of the formula IV

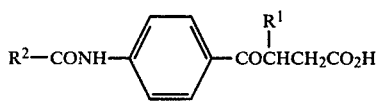

where $R^1$ and $R^2$ have the meanings given for formula I, is cyclized with hydrazine.

This cyclization reaction with hydrazine—the latter preferably being employed as the hydrate—is advantageously carried out in a solvent which is inert under the reaction conditions, especially a lower alcohol, such as methanol, ethanol or propanol, a cyclic aliphatic ether, such as tetrahydrofuran or dioxane, or a dialkylformamide, such as dimethylformamide, at from 60° to 150° C., preferably from 80° to 120° C. As a rule, from 1 to 1.2 moles of hydrazine or hydrazine hydrate are employed per mole of compound of the formula IV.

The starting compounds of the formula IV can be prepared by a process wherein an aminoacid of the formula V

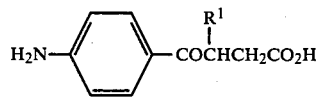

where $R^1$ has the meanings given for formula I, is acylated with an acylating agent of the formula III $R^2COY$     III where $R^2$ and Y have the above meanings, under the conditions stated above.

The compounds of the formula IV, where $R^1$ is hydrogen and $R^2$ has the corresponding meanings given above, can also be obtained by a process wherein an anilide of the formula VI

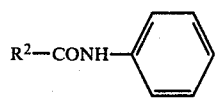    VI where $R^2$ has the meanings given for the case of $R^1$ being hydrogen, is reacted with succinic anhydride in the presence of aluminum chloride under the conditions of a Friedel-Crafts acylation.

This Friedel-Crafts acylation can be carried out in a solvent, for example carbon disulfide, at from 0° to 60° C. It can also be carried out in a dimethylformamide/aluminum chloride melt at from 50° to 120° C., preferably from 60° to 90° C. It is advantageous to employ about 10 moles of aluminum chloride and about 2.5 moles of dimethylformamide for 1 mole of succinic anhydride and 1 mole of anilide of the formula VI.

The compounds of the formula IV, where $R^1$ is methyl and $R^2$ has the meanings given above for when $R^1$ is alkyl, can also be prepared by a process wherein an anilide of the formula VI, where $R^2$ has the meanings given for when $R^1$ is alkyl, is reacted with citraconic anhydride in the presence of aluminum chloride under the conditions of a Friedel-Crafts reaction and the resulting 3-(p-acylaminobenzoyl)-crotonic acid of the formula VII

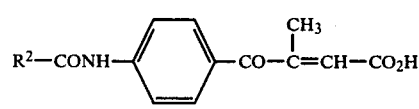

is treated with zinc in glacial acetic acid. This reaction can be carried out, for example, under the conditions which are described in German Laid-Open Application DOS No. 2,150,436 for the preparation of a 3-(p-alkanoylaminobenzoyl)-butyric acid of the formula VIII

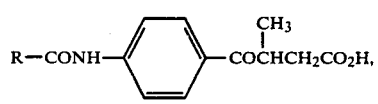

R = alkyl from an anilide of the formula IX

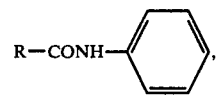

R = alkyl.

Dihydropyridazinones of the formula I, where $R^2$ is halogen-substituted cycloalkyl, are preferably obtained by reacting a compound of the formula II with an acylating agent of the formula III or by cyclizing an acylamino compound of the formula IV with hydrazine.

the compounds of the formula II and the compounds of the formula V, used as starting materials, are known or can be prepared, for example, under the conditions described in German Laid-Open Applications DOS No. 1,670,158 and DOS No. 2,150,436, or in U.S. Patents Nos. 3,824,271 and 3,888,901.

Examples of compounds according to the invention, which are obtained by the processes mentioned, are: 6-(p-cyclopropylcarbonylaminophenyl)-4,5-dihydro-3(2H)-pyridazinone, 6-(p-cyclopropylcarbonylaminophenyl)-4,5-dihydro-5-methyl-3(2H)-pyridazinone, 4,5-dihydro-6-[p-(1-methylcyclopropylcarbonylamino)-phenyl]-3(2H)-pyridazinone, 4,5-dihydro-5-methyl-6-[p-(1-methylcyclopropylcarbonylamino)-phenyl]-3(2H)-pyridazinone, cis- and trans-4,5-dihydro-6-[p-(2-methylcyclopropylcarbonylamino)-phenyl]-3(2H)- pyridazinone, cis- and trans-4,5-dihydro-5-methyl-6-[p-(2-methylcyclopropylcarbonylamino)-phenyl]-3(2H)-pyridazinone, 4,5-dihydro-6-[p-(2,2-dimethylcyclopropylcarbonylamino)-phenyl]-3(2H)-pyridazinone, 4,5-dihydro-6-[p-(2,2-dimethylcyclopropylcarbonylamino)-phenyl]-5-methyl-3(2H)-pyridazinone, cis- and trans-4,5-dihydro-5-methyl-6-[p-(2,2,3-trimethylcyclopropylcarbonylamino)-phenyl]-3(2H)-pyridazinone, 6-[p-(1-chlorocyclopropylcarbonylamino)-phenyl]-4,5-dihydro-3(2H)-pyridazinone, 6-[p-(1-chlorocyclopropylcarbonylamino)-phenyl]-4,5-dihydro-5-methyl-3(2H)-pyridazinone, cis- and trans-6-[p-(2-bromocyclopropylcarbonylamino)-phenyl]-4,5-dihydro-3(2H)-pyridazinone, cis- and trans-6-[p-(2-bromocyclopropylcarbonylamino)-phenyl]-4,5-dihydro-5-methyl-3(2H)-pyridazinone, 6-[p-(2,2-dichlorocyclopropylcarbonylamino)-phenyl]-4,5-dihydro-3(2H)-pyridazinone, 6-[p-(2,2-dichlorocyclopropylcarbonylamino)-phenyl]-4,5-dihydro-5-methyl-3(2H)-pyridazinone, 6-[p-(2,2-dibromocyclopropylcarbonylamino)-phenyl]-4,5-dihydro-5-methyl-3(2H)-pyridazinone, 6-[p-(2,2-dichloro-1-methylcyclopropylcarbonylamino)-phenyl]-4,5-dihydro-3(2H)-pyridazinone, 6-[p-(2,2-dichloro-1-methylcyclopropylcarbonylamino)-phenyl]-4,5-dihydro-5-methyl-3(2H)-pyridazinone, 6-(p-cyclobutylcarbonylaminophenyl)-4,5-dihydro-3(2H)-pyridazinone, 6-(p-cyclobutylcarbonylaminophenyl)-4,5-dihydro-5-methyl-3(2H)-pyridazinone, 4,5-dihydro-5-methyl-6-[p-(1-methylcyclobutylcarbonylamino)-phenyl]-3(2H)-pyridazinone, cis- and trans-4,5-dihydro-5-methyl-6-[p-(2-methylcyclobutylcarbonylamino)-phenyl]-3(2H)-pyridazinone, cis- and trans-4,5-dihydro-5-methyl-6-[p-(3-methylcyclobutylcarbonylamino)-phenyl]-3(2H)-pyridazinone, 6-[p-(1-chlorocyclobutylcarbonylamino)-phenyl]-4,5-dihydro-3(2H)-pyridazinone, 6-[p-(1-chlorocyclobutylcarbonylamino)-phenyl]-4,5-dihydro-5-methyl-3(2H)-pyridazinone, cis- and trans-6-[p-(2-chlorocyclobutylcarbonylamino)-phenyl]-4,5-dihydro-5-methyl-3(2H)-pyridazinone, cis- and trans-6-[p-(3-chlorocyclobutylcarbonylamino)-phenyl]-4,5-dihydro-3(2H)-pyridazinone, cis- and trans-6-[p-(3-chlorocyclobutylcarbonylamino)-phenyl]-4,5-dihydro-5-methyl-3(2H)-pyridazinone, 6-[p-(1-bromocyclobutylcarbonylamino)-phenyl]-4,5-dihydro-5-methyl-3(2H)-pyridazinone, 4,5-dihydro-5-methyl-6-[p-(2,2,3,3-tetrafluorocyclobutylcarbonylamino)-phenyl]-3(2H)-pyridazinone, 6-[p-(1-bromo-3,3-dimethylcyclobutylcarbonylamino)-phenyl]-4,5-dihydro-5-methyl-3(2H)-pyridazinone, 6-(p-cyclopentylcarbonylaminophenyl)-4,5-dihydro-5-methyl-3(2H)-pyridazinone, 4,5-dihydro-5-methyl-6-[p-(1-methylcyclopentylcarbonylamino)-phenyl]-3(2H)-pyridazinone, 6-[p-(1-chlorocyclopentylcarbonylamino)-phenyl]-4,5-dihydro-5-methyl-3(2H)-pyridazinone, 6-[p-(3,4-dichlorocyclopentylcarbonylamino)-phenyl]-4,5-dihydro-5-methyl-3(2H)-pyridazinone, 6-(p-cyclohexylcarbonylaminophenyl)-4,5-dihydro-5-methyl-3(2H)-pyridazinone and 6-[p-(1-chlorocyclohexylcarbonylamino)-phenyl]-4,5-dihydro-5-methyl-3(2H)-pyridazinone.

It is to be noted that the compounds of the formula I, where $R^1$ is not hydrogen, have an asymmetrical carbon atom in the 5-position and are obtained as racemates. The present invention also encompasses the enantiomers. If a separation is desired, it is advantageously carried out at the stage of a compound of the formula II, using conventional methods, for example the formation of diastereomeric salts with optically active auxiliary acids, such as dibenzoyltartaric acid or camphor-10-sulfonic acid.

Where $R^2$ has a suitable meaning, for example 2-methylcyclopropyl, the compounds of the formula I furthermore exhibit geometrical cis-trans isomerism. The present invention encompasses the cis- and trans-isomers and their mixtures. The pure cis-compounds or trans-compounds are obtained by using pure starting compounds or by separating the cis-trans mixtures by crystallization.

The novel dihydropyridazinones of the formula I exhibit thrombocyte aggregation-inhibiting and blood pressure-lowering properties. They are useful as antihypertensives and for the prophylaxis and therapy of thrombo-embolic disorders.

The advantageous thrombocyte aggregation-inhibiting action can be shown by comparison with acetylsalicylic acid, for example by experiments on collagen-induced aggregation of human thrombocytes. The blood pressure-lowering action can be demonstrated, for example, on rats under urethane narcosis; the reference substance can be, for example, dihydralazine.

Specifically, the following methods were used to investigate the pharmacodynamic properties.

1. Inhibition of collagen-induced aggregation of rat thrombocytes ex vivo.

The substances are administered orally to groups of 10–15 male Sprague-Dawley rats (200–250 g). 1 hour after administration, blood is taken under ether narcosis and thrombocyte-rich plasma is isolated by centrifuging (300 g, 10 minutes at 4° C.). The thrombocyte aggregation is measured photometrically, with addition of magnesium chloride (final concentration 100 millimoles/l) and of collagen Stago (final concentration 0.02 mg/ml), in a born Aggregometer Mk 3. The maximum change in extinction per second is used as the measure of the aggregation.

The ED 33% is determined as the dose which inhibits the collagen-induced thrombocyte aggregation by 33%.

2. Anti-hypertensive action on spontaneously hypertonic rats.

The substances are administered orally to male, spontaneously hypertonic, Okamoto rats (4–8 animals per dose; weight 270–360 g). The systolic blood pressure is measured non-surgically, before and 2 hours after administration, on the tails of the rats, by means of piezoelectric recorders.

The ED 20% is determined as the dose which lowers the systolic pressure by 20%, with due account taken of the values found on untreated control animals.

The results obtained are shown in Table 1 below, in respect of which the following should be noted:

The recognized agents acetylsalicylic acid (ASA) and dihydralazine are used as comparative substances, having a relative activity (R.A.) of 1. Comparison is also made with a structurally similar compound of the prior art, namely 6-[p-(2-chloropropionylamino)-phenyl]-4,5-dihydro-5-methyl-3(2H)-pyridazinone (compound $V_1$), which has already been shown to be very active.

The numeral data obtained show that all the novel compounds listed in the Table are substantially more effective than the commercial compounds in respect of at least one of the effects investigated.

TABLE 1

| Compound of Example No. | Inhibition of thrombocyte aggregation | | Anti-hypertensive effect | |
|---|---|---|---|---|
| | ED 33% | R.A. | ED 20% | R.A. |
| 1, 2 | 0.357 | 652.66 | 1.79 | 3.83 |
| 3 | 0.240 | 970.83 | 0.155 | 44.19 |
| 14 | 16.9 | 13.79 | 0.681 | 10.06 |
| 15 | 2.00 | 116.5 | 0.168 | 40.77 |
| 16 | >10.0 | <23.30 | 2.67 | 2.57 |
| $V_1$ | 0.82 | 284.15 | 1.16 | 5.91 |
| ASA | 233 | 1.00 | — | — |
| Dihydralazine | — | — | 6.85 | 1.00 |

Accordingly, the present invention also relates to therapeutic agents or formulations which contain a compound of the formula I as the active compound, together with conventional pharmaceutical carriers and diluents, and to the use of these compounds in the treatment of high blood pressure and of thrombo-embolic disorders.

The therapeutic agents or formulations are prepared in a known manner, using the conventional carriers or diluents, the conventional pharmaceutical auxiliaries, and a suitable dose of the active compound, in accordance with the desired route of administration. Appropriate doses for man are from 1 to 100 mg, preferably from 5 to 50 mg, oral administration being preferred.

Examples of forms suitable for oral administration are tablets, film tablets, dragees, capsules, pills, powders, solutions, suspensions and depot forms.

For practical use, the compounds to be employed according to the invention are compounded with the conventional pharmaceutical carriers. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, such as corn starch, alginic acid or polyvinylpyrrolidone, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers (cf. L. G. Godman and A. Gilman, The Pharmacological Basis of Therapeutics).

Correspondingly, dragees can be prepared from cores, prepared similarly to the tablets, and coatings containing the conventional agents, for example polyvinylpyrrolidone or shellac, gum arabic, talc, titanium dioxide or sugar. The dragee coating can also consist of several layers, and the auxiliaries mentioned above in connection with tablets can be used.

The Examples which follow illustrate the preparation of the novel 6-(p-acylaminophenyl)-4,5-dihydro-3(2H)-pyridazinones.

EXAMPLE 1

6.0 g (31.7 millimoles) of 6-(p-aminophenyl)-4,5-dihydro-3(2H)-pyridazinone and 4.0 g (38.3 millimoles) of cyclopropanecarboxylic acid chloride in 100 ml of absolute toluene are kept for 6 hours at 80° C. The product is filtered off at 10° C., washed first with toluene and then with water, and recrystallized from dimethylformamide/water. 5.0 g (61% of theory) of 6-(p-cyclopropylcarbonylaminophenyl)-4,5-dihydro-3(2H)-pyridazinone are obtained as colorless crystals, of melting point 272°–273° C.

Analysis for $C_{14}H_{15}N_3O_2$: calculated: C 65.4 H 5.9 N 16.3% found: C 65.0 H 5.9 N 16.5%

EXAMPLE 2

(a) 3.2 g (30.6 millimoles) of cyclopropanecarboxylic acid chloride, dissolved in 20 ml of absolute tetrahydrofuran, are added dropwise, at room temperature, to a stirred solution of 5.0 g (25.9 millimoles) of 3-(p-aminobenzoyl)-propionic acid in 100 ml of absolute tetrahydrofuran; a precipitate forms. The reaction mixture is then kept for 7 hours under reflux. The product is filtered off at 10° C., washed with water and dried under reduced pressure at 50° C. 5.1 g (75% of theory) of 3-(p-cyclopropylcarbonylaminobenzoyl)-propionic acid are obtained as yellow crystals, of melting point 229°–230° C. (after recrystallization from ethanol/water).

Analysis for $C_{14}H_{15}NO_4$: calculated: C 64.4 H 5.8 N 5.4% found: C 64.5 H 5.9 N 5.3%

(b) 2.0 g (7.7 millimoles) of 3-(p-cyclopropylcarbonylaminobenzoyl)-propionic acid, 0.45 g (9.0 millimoles) of hydrazine hydrate and 20 ml of ethanol are refluxed for 6 hours. The product is filtered off at 10° C. and recrystallized from dimethylformamide/water, giving 1.35 g (68% of theory) of 6-(p-cyclopropylcarbonylaminophenyl)-4,5-dihydro-3(2H)-pyridazinone, as colorless crystals, identical with the compound from Example 1.

EXAMPLE 3

6.0 g (29.5 millimoles) of 6-(p-aminophenyl)-4,5-dihydro-5-methyl-3(2H)-pyridazinone, 3.4 g (32.5 millimoles) of cyclopropanecarboxylic acid chloride and 100 ml of absolute toluene are kept for 6 hours at 80° C. The product is filtered off at 10° C., washed first with toluene and then with water, and recrystallized from dimethylformamide/water. 6.8 g (85% of theory) of 6-(p-cyclopropylcarbonylaminophenyl)-4,5-dihydro-5-methyl-3(2H)-pyridazinone are obtained as beige crystals, of melting point 267°–268° C.

Analysis for $C_{15}H_{17}N_3O_2$: calculated: C 66.4 H 6.3 N 15.5% found: C 66.3 H 6.5 N 15.7%

EXAMPLE 4

6.0 g (29.5 millimoles) of 6-(p-aminophenyl)-4,5-dihydro-5-methyl-3(2H)-pyridazinone are dissolved in 150 ml of absolute tetrahydrofuran by stirring and heating to 60° C. 4.2 g (35.4 millimoles) of 1-methylcyclopropanecarboxylic acid chloride are added dropwise to the above solution at 60° C., and the reaction mixture is then stirred for 7 hours at the reflux temperature. The product is filtered off at 10° C., washed with water and recrystallized twice from dimethylformamide/water. 5.5 g (65% of theory) of 4,5-dihydro-5-methyl-6-[p-(1-methylcyclopropylcarbonylamino)-phenyl]-3(2H)-pyridazinone are obtained as almost colorless crystals, of melting point 235°–237° C.

Analysis for $C_{16}H_{19}N_3O_2$: calculated: C 67.3 H 6.7 N 14.7% found: C 67.2 H 6.7 N 14.9%

EXAMPLE 5

5.0 g (26.4 millimoles) of 6-(p-aminophenyl)-4,5-dihydro-3(2H)-pyridazinone, 4.2 g (31.7 millimoles) of 2,2-dimethylcyclopropanecarboxylic acid chloride in 100 ml of absolute tetrahydrofuran are refluxed for 7 hours. The mixture is concentrated to about 50 ml and the product is filtered off at 10° C., washed with water and recrystallized from dimethylformamide/water. 5.2 g (68% of theory) of 4,5-dihydro-6-[p-(2,2-dimethylcyclopropylcarbonylamino)-phenyl]-3(2H)-pyridazinone quarter-hydrate are obtained as almost colorless crystals, of melting point 213°–214° C.

Analysis for $C_{16}H_{19}N_3O_2 \cdot \frac{1}{4}H_2O$: calculated: C 66.3 H 6.8 N 14.5% found: C 66.5 H 6.8 N 14.3%

EXAMPLE 6

Using a method similar to that of Example 4, 6.0 g (29.5 millimoles) of 6-(p-aminophenyl)-4,5-dihydro-5-methyl-3(2H)-pyridazinone are reacted with 4.7 g (35.4 millimoles) of 2,2-dimethylcyclopropanecarboxylic acid chloride in 150 ml of absolute tetrahydrofuran. The mixture is concentrated to about 70 ml, water is added and the product is filtered off, washed with water and recrystallized twice from dimethylformamide/water, giving 5.8 g (66% of theory) of 4,5-dihydro-6-[p-(2,2-dimethylcyclopropylcarbonylamino)-phenyl]-5-methyl-3(2H)-pyridazinone as colorless crystals, of melting point 222°–223° C.

Analysis for $C_{17}H_{21}N_3O_2$: calculated: C 68.2 H 7.1 N 14.0% found: C 68.2 H 7.4 N 13.7%

EXAMPLE 7

A solution of 4.45 g (32.0 millimoles) of 1-chlorocyclopropanecarboxylic acid chloride in 20 ml of absolute tetrahydrofuran is added dropwise to a stirred suspension of 5.0 g (26.4 millimoles) of 6-(p-aminophenyl)-4,5-dihydro-3(2H)-pyridazinone in 100 ml of absolute tetrahydrofuran. The mixture is then stirred for 20 hours at room temperature followed by 1 hour under reflux. The product is filtered off at 10° C., washed first with tetrahydrofuran and then with water, and recrystallized from dimethylformamide/water. 6.3 g (82% of theory) of 6-[p-(1-chlorocyclopropylcarbonylamino)-phenyl]-4,5-dihydro-3(2H)-pyridazinone are isolated as colorless crystals, of melting point 231°–232° C.

Analysis for $C_{14}H_{14}ClN_3O_2$: calculated: C 57.6 H 4.8 Cl 12.2 N 14.4% found: C 57.8 H 5.0 Cl 11.8 N 14.7%

EXAMPLE 8

(a) 3.9 g (28.1 millimoles) of 1-chlorocyclopropanecarboxylic acid chloride are added, with stirring, to 4.5 g (23.3 millimoles) of 3-(p-aminobenzoyl)-propionic acid in 100 ml of absolute tetrahydrofuran. The reaction mixture is then stirred for 20 hours at room temperature, followed by 7 hours under reflux. A small amount of solid is filtered off and discarded, and the filtrate is concentrated. The residue obtained is recrystallized from ethyl acetate, giving 3.4 g (49% of theory) of 3-[p-(1-chlorocyclopropylcarbonylamino)-benzoyl]-propionic acid as colorless crystals, of melting point 178°–179° C.

Analysis for $C_{14}H_{14}ClNO_4$: calculated: C 56.9 H 4.8 Cl 12.0 N 4.7% found: C 57.0 H 4.6 Cl 11.6 N 4.5%

(b) 2.75 g (9.3 millimoles) of 3-[p-(1-chlorocyclopropylcarbonylamino)-benzoyl]-propionic acid, 0.47 g (9.4 millimoles) of hydrazine hydrate and 20 ml of ethanol are refluxed for 6 hours. The product is filtered off at 10° C., washed with ethanol and dried under reduced pressure at 50° C., giving 2.5 g (92% of theory) of 6-[p-(1-chlorocyclopropylcarbonylamino)-phenyl]-4,5-dihydro-3(2H)-pyridazinone as colorless crystals (identical with the compound from Example 7).

EXAMPLE 9

5.0 g (24.6 millimoles) of 6-(p-aminophenyl)-4,5-dihydro-5-methyl-3(2H)-pyridazinone are dissolved in 100 ml of absolute tetrahydrofuran by stirring and heating to 60° C. The solution is allowed to cool to room temperature, 4.15 g (29.9 millimoles) of 1-chlorocyclopropanecarboxylic acid chloride are added dropwise and the reaction solution is then stirred for 6 hours at room temperature. It is then concentrated to half its volume and 200 ml of water are added. The precipitate which forms is filtered off, washed with water and recrystallized from methanol, giving 5.5 g (73% of theory) of 6-[p-(1-chlorocyclopropylcarbonylamino)-phenyl]-4,5-dihydro-5-methyl-3(2H)-pyridazinone as colorless crystals, of melting point 189°–190° C.

Analysis for $C_{15}H_{16}ClN_3O_2$:
calculated: C 58.9 H 5.3 Cl 11.6 N 13.7% found: C 59.0 H 5.3 Cl 11.9 N 13.8%

EXAMPLE 10

6.0 g (31.7 millimoles) of 6-(p-aminophenyl)-4,5-dihydro-3(2H)-pyridazinone and 6.6 g (38.1 millimoles) of 2,2-dichlorocyclopropanecarboxylic acid chloride in 100 ml of absolute tetrahydrofuran are refluxed for 6 hours. The product is filtered off at 10° C., washed first with tetrahydrofuran and then with water, and recrystallized from dimethylformamide/water. 7.5 g (73% of theory) of 6-[p-(2,2-dichlorocyclopropylcarbonylamino)-phenyl]-4,5-dihydro-3(2H)-pyridazinone are obtained as colorless crystals, of melting point 267°–268° C.

Analysis for $C_{14}H_{13}Cl_2N_3O_2$: calculated: C 51.6 H 4.0 Cl 21.7 N 12.9% found: C 51.3 H 4.1 Cl 21.6 N 12.9%

EXAMPLE 11

5.0 g (24.6 millimoles) of 6-(p-aminophenyl)-4,5-dihydro-5-methyl-3(2H)-pyridazinone are dissolved in 100 ml of absolute tetrahydrofuran by stirring and heating to 60° C. The solution is allowed to cool to room temperature, 5.15 g (29.7 millimoles) of 2,2-dichlorocyclopropanecarboxylic acid chloride, dissolved in 10 ml of absolute tetrahydrofuran, are added dropwise and the mixture is then stirred for 6 hours under reflux. Thereafter it is concentrated to about 50 ml and the product is filtered off at 10° C., washed with water and recrystallized from dimethylformamide/water. 5.0 g (60% of theory) of 6-[p-(2,2-dichlorocyclopropylcarbonylamino)-phenyl]-4,5-dihydro-5-methyl-3(2H)-pyridazinone are obtained as colorless crystals, of melting point 252°–253° C.

Analysis for $C_{15}H_{15}Cl_2N_3O_2$: calculated: C 53.0 H 4.4 Cl 20.8 N 12.4% found: C 53.0 H 4.4 Cl 20.7 N 12.5%

EXAMPLE 12

Example 1 is repeated using 2,2-dichloro-1-methylcyclopropanecarboxylic acid chloride (8.9 g (47.5 millimoles)) in place of cyclopropanecarboxylic acid chloride; after recrystallization from dimethylformamide/water, 4.0 g (37% of theory) of 6-[p-(2,2-dichloro-1-methylcyclopropylcarbonylamino)-phenyl]-4,5-dihydro-3(2H)-pyridazinone are obtained as colorless crystals, of melting point 209°–210° C.

Analysis for $C_{15}H_{15}Cl_2N_3O_2$: calculated: C 53.0 H 4.4 Cl 20.8 N 12.4% found: C 52.9 H 4.5 Cl 20.4 N 12.4%

EXAMPLE 13

4.0 g (21.1 millimoles) of 6-(p-aminophenyl)-4,5-dihydro-3(2H)-pyridazinone of trans-2-bromocyclopropanecarboxylic acid chloride, 4.3 g (23.4 millimoles) and 100 ml of absolute tetrahydrofuran are kept for 20 hours at room temperature and then refluxed for 6 hours. The product is filtered off at 10° C., washed with water and recrystallized from dimethylformamide/water. 4.1 g (58% of theory) of trans-6-[p-(2-bromocyclopropylcarbonylamino)-phenyl]-4,5-dihydro-3(2H)-pyridazinone are obtained as colorless crystals, of melting point 260°–261° C. (with decomposition).

Analysis for $C_{14}H_{14}BrN_3O_2$:
calculated: C 50.0 H 4.2 Br 23.8 N 12.5% found: C 49.8 H 4.2 Br 24.3 N 12.7%

EXAMPLE 14

4.0 g (19.7 millimoles) of 6-(p-aminophenyl)-4,5-dihydro-5-methyl-3(2H)-pyridazinone are dissolved in 100 ml of absolute tetrahydrofuran by heating to 60° C., whilst stirring. The solution is allowed to cool to room temperature, 4.0 g (21.8 millimoles) of trans-2-bromocyclopropanecarboxylic acid chloride are added dropwise and the mixture is stirred for 20 hours at room temperature and then for 1 hour under reflux. Thereafter it is concentrated to about 50 ml, water is added and the product is filtered off. It is washed with water and recrystallized from dimethylformamide/water, giving 6.5 g (94% of theory) of trans-6-[p-(2-bromocyclopropylcarbonylamino)-phenyl]-4,5-dihydro-5-methyl-3(2H)-pyridazinone as colorless crystals of melting point 238°–239° C. (with decomposition).

Analysis for $C_{15}H_{16}BrN_3O_2$: calculated: C 51.4 H 4.6 Br 22.8 N 12.0% found: C 51.6 H 4.6 Br 22.4 N 11.8%

EXAMPLE 15

If, in place of cyclopropanecarboxylic acid chloride, cyclobutanecarboxylic acid chloride (3.9 g (32.9 millimoles)) is employed in Example 3, and the product is recrystallized from ethanol/water, 2.6 g (31% of theory) of 6-(p-cyclobutylcarboylaminophenyl)-4,5-dihydro-5-methyl-3(2H)-pyridazinone are obtained as colorless crystals, of melting point 163°–164° C.

Analysis for $C_{16}H_{19}N_3O_2$: calculated: C 67.3 H 6.7 N 14.7% found: C 66.9 H 6.6 N 14.8%

The compounds of Examples 16 to 18, listed in Table 2 below, are prepared by the method described in Example 3.

| 1. Tablets: | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10% strength aqueous solution of the polyvinylpyrrolidone, forced through a 1.0 mm mesh sieve and dried at 50° C. The granules obtained are mixed with the polyethylene glycol (mean molecular weight 4,000), hydroxypropylmethylcellulose, talc and magnesium stearate, and the mixture is pressed to give tablets each weighing 240 mg.

| 2. Example of dragees: | |
|---|---|
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The mixture of the active compound, lactose and corn starch is moistened with an 8% strength aqueous solution of the polyvinylpyrrolidone, granulated by passing through a 1.5 mm mesh sieve, dried at 50° C. and forced through a 1.0 mm mesh sieve. The granules thus obtained are mixed with magnesium stearate and the mixture is pressed to give dragee cores. These cores are then coated in a conventional manner with a shell essentially consisting of sugar and talc.

We claim:
1. A 6-(p-acylaminophenyl)-4,5-dihydro-3(2H)-pyridazinone of the formula I

TABLE 2

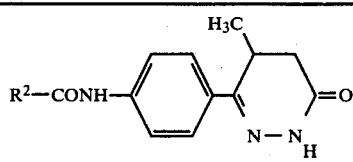

| Example | R² | Melting point [°C.] | | Analysis (%) | | | |
|---|---|---|---|---|---|---|---|
| | | | | C | H | Cl | N |
| 16 | H₃C–▷– | 258–260 (dimethylformamide/water) | calc. found | 67.3 66.9 | 6.7 6.8 | — — | 14.7 14.7 |
| 17 | Cl₂C(CH₃)– | 219–220 (dimethylformamide/water) | calc. found | 54.3 54.5 | 4.8 4.8 | 20.0 19.6 | 11.9 12.1 |
| 18 | ⬡– | 231–232 (propanol/water) | calc. found | 69.0 69.1 | 7.4 7.3 | — — | 13.4 13.1 |

Examples of formulations prepared in a conventional manner:

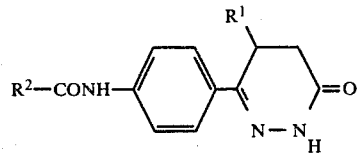

where $R^1$ is hydrogen or methyl, $R^2$ is unsubstituted cyclopropyl.

2. A therapeutic agent for treating high blood pressure and/or thrombotic diseases which comprises: a therapeutically effective amount of a compound of the formula I as described in claim 1 together with a pharmacological acceptable carrier or diluent.

3. A process for treating high blood pressure and/or thrombotic diseases which comprises: orally administering to the subject to be treated a composition in dosage form comprising from 1 to 100 mg. of a compound of the formula I of claim 1 and a pharmacologically acceptable carrier or diluent.

* * * * *